United States Patent
Carlsson et al.

[11] Patent Number: 6,022,561
[45] Date of Patent: Feb. 8, 2000

[54] BILAYERS PREPARATIONS

[75] Inventors: Anders Carlsson; Bengt Herslöf, both of Stockholm; Snezana Petrovic-Källholm, Spånga, all of Sweden

[73] Assignee: Scotia Lipidteknik AB, Stockholm, Sweden

[21] Appl. No.: 09/141,058

[22] Filed: Aug. 27, 1998

Related U.S. Application Data

[63] Continuation of application No. 08/676,139, filed as application No. PCT/SE95/00116, Feb. 6, 1995.

[30] Foreign Application Priority Data

| Feb. 4, 1994 | [SE] | Sweden | 9400368 |
| Jul. 12, 1994 | [SE] | Sweden | 9402455 |

[51] Int. Cl.$^7$ .................................................. A61K 9/127
[52] U.S. Cl. ...................... 424/450; 424/401; 424/427; 424/430; 424/434; 424/436
[58] Field of Search .................................. 426/450, 401, 426/427, 430, 434, 436

[56] References Cited

U.S. PATENT DOCUMENTS

| 5,151,272 | 9/1992 | Engstrom . |
| 5,234,767 | 8/1993 | Wallach . |
| 5,236,709 | 8/1993 | Soma . |
| 5,382,430 | 1/1995 | Soma . |

FOREIGN PATENT DOCUMENTS

| 0009842 | 4/1980 | European Pat. Off. . |
| 0249561 | 12/1987 | European Pat. Off. . |

OTHER PUBLICATIONS

Foley Chemical Abstracts 108, 200519, 1988.
Sprague Chemical Abstracts 100, 64424, 1983.

*Primary Examiner*—Gollamudi S. Kishore
*Attorney, Agent, or Firm*—Hoffmann & Baron, LLP

[57] ABSTRACT

A galactolipid material from wheat, produced by extraction of crushed wheat grains and subsequent chromatography of the extracted material, and having a content of DGDG of 51.5%, was mixed with the polar solvents, water and glycerol in order to test the swellability. The samples, prepared in glass tubes, were alternately mixed with a rod and centrifugated at room temperature until homogeneous. The samples were inspected as to physical appearance after storing for at least a week at room temperature.
Results:

20% (w/w) of galactolipid material in water gave a slightly yellow, highly viscous dispersion. Small liposomes could be observed in a polarizing microscope. At higher galactolipid concentrations a stiff gel was formed.

10% (w/w) of the same lipid material in anhydrous glycerol resulted in the formation of an opaque, highly viscous gel.

19 Claims, 2 Drawing Sheets

BILAYERS PREPARATIONS

This is a continuation application of application Ser. No. 08/676,139 filed on Jul. 15, 1996 now abandoned which was the national stage of International Application No. PCT/SE95/00116, filed Feb. 6, 1995.

TECHNICAL FIELD

This invention relates to bilayer preparations of lipids in polar solvents. These preparations are suitable for use as carriers for an active substance in a pharmaceutical composition, but also in nutritional, cosmetical, food and agricultural products.

BACKGROUND OF THE INVENTION

There has been only a limited use for natural amphiphilic lipid excipients in pharmaceutical and cosmetic manufacture. The reasons are in many cases lack of raw material and high production costs, as well as poor performance of the final lipid material.

Among the natural polar, bilayer-forming lipids, i.e. amphiphilic lipids, the phospholipids are the most common in pharmaceutical and cosmetical use. Due to their bilayer-forming ability these polar lipids may be used for the formation of different kinds of aggregates and particles, such as vesicles and liquid crystals, which have found many technical applications.

However, there has only been a limited use of lipid gels based on phospholipids in pharmaceutical technology, mainly due to insufficient gel-forming abilities and poor chemical stability. The predominant natural polar, bilayer-forming lipid used so far, phosphatidylcholine from egg yolk or soybean, is slightly too lipophilic for optimal swelling in water and formation of the flexible bilayers which build up the liquid crystalline lamellar structures.

Since liposomes are dispersions of bilayer or lamellar phases in excess aqueous solution, it is thus not optimal to use phospholipid-based lamellar phases when forming liposomes. The swelling procedure is slow and a high input of mechanical energy is often required in order to form liposomes and vesicles from a phospholipid material within a reasonable period of time.

Natural phospholipids, such as phosphatidylcholine from egg yolk, are highly unsaturated. Unsaturation of the acyl chains of the phospholipid is a prerequisite for the formation of a liquid crystalline lamellar phase at room temperature. However, this also means that bilayer membranes formed by natural phospholipids possess a high permeability towards water-soluble drugs, since the acyl chains are in a disordered, fluid state. Liposomes made of natural phospholipids are thus characterised by a low encapsulation efficiency due to the leakage of incorporated drug across the liposomal bilayers. Normally, if drugs are to be incorporated into natural phospholipid liposomes, they must be stabilised by the addition of large amounts of cholesterol, 30–50 mole % of the total lipid composition.

This also applies to active substances other than drugs which for some reason are to be incorporated into liposomes or other bilayer structures.

Phospholipid-based vesicles and liposomes usually have a very short life-time after being introduced into circulation in the bloodstream. The rapid clearance from the blood is due to their uptake by the reticulo-endothelial system (RES) of the liver and the spleen. In order to overcome this, liposomes may be sterically stabilised by the addition of gangliosides, containing several carbohydrate units, or hydrophilic polymers, such as polyethylene oxide or pullulan. The latter agents are normally covalently bonded to phosphatidylethanolamine. In principle, this approach is very efficient and the modified liposomes may escape uptake by RES. In practice, it is however disadvantageous to add additional components, either natural and rare, and therefore expensive, or synthetic, and therefore not necessarily biocompatible, to the liposomal formulation, both from a safety and an economical point of view.

PRIOR ART

The use of phospholipids and other polar lipids for the preparation of liquid crystals and liposomes is well-known.

EP-B1-0 126 751 discloses a controlled release composition which may include an amphiphilic substance such as galactolipids, phospholipids and monoglycerides. This patent is directed to cubic and reverse hexagonal liquid crystalline phases that are stable in excess aqueous solution.

WO 91/11993 discloses an alcoholic aqueous gel-type phospholipid composition. The alcohol is ethanol, 1-propanol or 2-propanol. The phospholipid content is in the range of 15 to 30% (w/w). Also disclosed is the use of the phospholipid composition to prepare liposomes by dilution with an aqueous solution, as well as topical preparations containing the gel.

Wo 91/04013 discloses hybrid paucilamellar lipid vesicles containing a phospho- or glycolipid and a non-ionic, anionic or zwitter-ionic surfactant in the lipid bilayers. Preferred glycolipids are cerebrosides, gangliosides and sulphatides, which all belong to the glycosphingolipid family.

Glycosylglycerides are a type of glycolipids which are well-known constituents of plant cell membranes. Two types based on galactose are very common, monogalactosyldiacylglycerol, MGDG, and digalactosyldiacylglycerol, DGDG, representing up to 40% of the dry weight of the thylakoid membranes.

Plant glycolipids have carbohydrate units, mainly of galactose, linked to glycerol. In MGDG the 1-position of the galactose ring has a β-link to glycerol, and in DGDG there is an α,1→6 bond between the sugars. A minor constituent is the plant sulpholipid, more correctly named sulphoquinovosyldiacyl-glycerol, SQDG, which contains a sulphonate rather than a hydroxyl group linked to carbon 6 of the terminal deoxyglucose residue. Most plant glycolipids can be described by the general formula

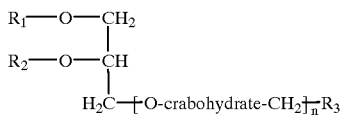

wherein $R_1$ and $R_2$ independently of each other are saturated or unsaturated fatty acid residues of 2–24 carbon atoms and 0–6 double bonds, further esterified hydroxyacids, that is estolides, or hydrogen; the carbohydrate is a monosaccharide unit; n=1–5; and $R_3$ is a hydroxyl or sulphonate group.

In investigating the interaction of glycosylglycerides with water and other polar solvents we have surprisingly found that specific glycolipid materials from cereals have a behaviour which makes said lipid materials suitable and simple to utilise as a carrier material for especially pharmaceutical compositions, and also for other formulations, such as cosmetical, agricultural, nutritional and food applications.

It is well known that lipids from cereals can interact with water due to their relatively high proportion of polar components to form a lamellar liquid crystalline phase (G. Jayasinghe et al., J. Disp. Sci. Technol., 1991, Vol. 12, pp. 443–451).

SE 9400368-8 discloses an industrially applicable process for preparing a glycolipid material from plants, preferably cereals, by means of extraction and chromatographic separations. The glycolipid material so prepared can be used as an amphiphilic material in pharmaceutical products, cosmetics and food.

DESCRIPTION OF THE INVENTION

The invention refers to a lipid-polar solvent bilayer-preperation consisting of 0.01–90% by weight, preferably 0.1–50%, of a bilayer-forming material in a polar solvent, characterised in that the bilayer-forming material is a galactolipid material from cereals consisting of at least 50% digalactosyldiacylglycerols, the remainder being other polar lipids.

In a preferred preparation the galactolipid material consists of about 70–80% digalactosyldiacylglycerols and 20–30% other polar lipids.

In another preferred preparation the galactolipid material consists of up to 100% digalactosyldiacylglycerols.

The digalactosyldiacylglycerols can be described by the general formula

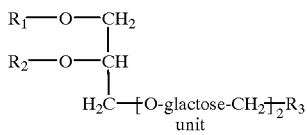

wherein $R_1$ and $R_2$ independently of each other are saturated or unsaturated fatty acid residues of 10–22 carbon atoms and 0–4 double bonds, or hydrogen; and $R_3$ is a hydroxyl or sulphonate group.

As preferred examples of fatty acid residues $R_1$ and $R_2$ can be mentioned naturally occurring fatty acyl groups, such as residues from the saturated acids palmitic ($C_{15}H_{31}CO$; 16:0) and stearic acid ($C_{17}H_{35}CO$; 18:0); from the monoun-saturated acid oleic acid ($C_{17}H_{33}CO$; 18:1); and from the polyunsaturated acids linoleic ($C_{17}H_{31}CO$; 18:2) and linolenic acid ($C_{17}H_{29}CO$; 18:3). The fatty acid residues can also contain hydroxyacids linked to the glycerol moiety with their hydroxyl groups esterified by further fatty acids, so called estolides.

The other polar lipids being part of the galactolipid material are a mixture of different glyco- and phospholipids, such as MGDG and phosphatidylcholines. The composition depends on the starting material and process used for the manufacture of the galactolipids.

The specific proportions of the components of the galactolipid material are not critical to the present invention as long as the content of DGDG is at least 50%. For many applications, however, the maximum benefits are realised by a high content of DGDG, the most important bilayer-forming component.

The galactolipid material can be extracted from almost any kind of plant material. Preferred plant materials are seeds and kernels from grains and cereals, for instance wheat, rye, oats, corn, rice, millet and sesame. Oat groats as well as wheat gluten have a high lipid concentration and are therefore of advantage to use in the process of preparation. The digalactosyldiacylglycerols of the galactolipid material can, if applicable, also be of synthetic origin.

The galactolipid material can be used as the polar lipid component in different organised solutions in which the lipid forms organised particles which are dispersed in a dilute randomly mixed solution, such as water, ethanol, glycerol, and other polar solvents, or mixtures thereof. The molecular geometry of DGDG resembles that of a truncated cone, which makes it possible to form flexible bilayers, that is lamellar liquid crystalline phases, and liposomes or vesicles, in aqueous solutions at physiological conditions.

The galactolipids can incorporate, that is swell, a large amount of a polar solvent such as water. Addition of water to the galactolipids leads to the spontaneous formation of a clear, viscous gel. The gel consists of a lamellar liquid crystalline phase, $L_\alpha$, in which lipid bilayers alternate with water in a lamellar structure. The $L_\alpha$ phase, easily detected by polarising light microscopy, is thermodynamically stable.

The swelling procedure is relatively slow due to the high viscosity of the lamellar liquid crystalline structure of the gel; however, it is possible to prepare clear, homogeneous samples containing as low as 10% (w/w) aqueous solution within 24 hours of slow agitation. Once the gel is formed, it is extremely stable towards chemical and microbial degradation and thus retains its physical integrity over an extended period of time.

Alternating layers of galactosylacylglycerols and polar solvent make the gel structure suitable for the incorporation of both lipophilic and hydrophilic bioactive substances. The lamellar structure has a relatively low viscosity at high shear rates which makes it possible to inject the gel by means of a syringe and a thin needle. The formulation can be used for the administration of drugs to various sites in humans and animals.

The polar solvents are preferably those that are biocompatible and approved for use in pharmaceutical, cosmetical or food formulations, such as water, ethanol, 1-propanol, 1,2-propanediol, glycerol and mixtures thereof.

According to a preferred embodiment the invention refers to a gel preparation comprising 25–90% by weight galactolipid material in a polar solvent.

Gels are easily prepared by adding a polar solvent such as water or an aqueous solution to the dry galactolipid material to give final lipid concentrations in the range of 25–90% (w/w). The mixtures are allowed to swell for 1–24 h at room temperature during gentle agitation in an appropriate container, e.g. a glass flask or an open beaker. The gels can also be prepared in glass tubes by mixing with a rod and centrifugation at room temperature.

The gels are pseudoplastic and remarkably stable with respect to physical appearance and microbial resistance. The viscosities of the gels are not significantly affected by moderate temperature changes and can, for example, therefore be transferred directly from the refrigerator to a syringe or other administration device.

It is further demonstrated that the gels of the invention can act as a slow release medium for incorporated active components in a more efficient way than gels made of phospholipids.

It is further demonstrated that the gels of the invention can incorporate a wide range of therapeutically active components, including lipophilic components, hydrochlorides, nitrates, amphiphiles, proteins and peptides.

According to another preferred embodiment the invention refers to a liposome preparation comprising 0.01–25% by weight galactolipid material in a polar solvent.

An intrinsic beneficial feature of the galactosylacylglycerols is the galactose units comprising the polar headgroup in each lipid molecule, which may sterically stabilise the liposomes, thus providing a prolonged life-span when injected into the bloodstream.

Liposomes, that is multilamellar vesicles, are prepared by direct hydration. A polar solvent, such as water or an aqueous solution, is added to the dry galactolipid material to give final lipid concentrations in the range of 0.01–25% (w/w). The mixtures are allowed to swell and equilibrate at room temperature for 1–24 h during gentle agitation, giving a liposomal dispersion. Liposomes can also be prepared by adding an excess of polar solvent to a gel prepared according to above, i.e. simply by dilution of the gel.

Unilamellar vesicles are prepared from a multilamellar vesicle dispersion by e.g. membrane extrusion or high-pressure homogenisation.

The unusual and surprising swelling properties of the galactolipid material make it remarkably easy to prepare liposomal dispersions and aqueous gels. For example, the spontaneous formation of liposomes in water is surprisingly useful in the preparation of liposomal dispersions even on a large scale. This is different from the procedures that are needed to form liposomes from phospholipids in which organic solvents, such as chloroform, ether, ethanol or a combination of these, are employed. The scaling-up of conventional phospholipid liposome preparations is a recognised problem, and many different procedures have been proposed to overcome these difficulties. This invention provides liposomal dispersions in a simple and reproducible way which can be of significant importance in the practical utilisation of liposomes, for example, as drug carriers.

It is demonstrated that the liposomes of the invention have a surprisingly good encapsulation efficiency.

It is further demonstrated that the liposomes of the invention surprisingly and significantly prolong the duration of active components even if the vesicles are created in a solution of these components and thus only a part of the said components are encapsulated by the vesicles.

It is further demonstrated that the liposomes of the invention reduce the toxicity of a potent anticancer drug without reduction in pharmacological effect.

The liposomes of the invention are bioadhesive and may therefore resolve the problem of adequate availability of an incorporated active component on certain biosurfaces, for example, cornea and mucosa.

The liposomes of the invention can incorporate a surprisingly wide range of active components, including lipophilic components, hydrochlorides, nitrates, amphiphiles, proteins, peptides and others.

Synthetic diglycosyldiacylglycerols based on galactose or any other monosaccharide unit, such as glucose, and natural glycosylglycerides, isolated from any source, based on other carbohydrate units than galactose, such as glucose, can be used in accordance with the invention.

Galactolipid material

Galactolipid materials have been prepared from different cereals as stated below, and used for making carrier preparations and pharmaceutical compositions of the invention as stated in the examples. In the specification % refers to % by weight if not otherwise stated. The proportion of the solvents in solvent mixtures is given in parts by volume.

Galactolipid material from oats 200 kg of oat kernels (Kungsörnen AB, Sweden) were ground and extracted with 1000 l of 95% ethanol at 70° C. for 3 h in an extraction tank under stirring. The slurry was centrifuged while still warm and separated from solid particles. The liquid fraction was evaporated at 60° C. which gave about 10 kg of a light brown oil.

The oil was applied to a stainless steel column containing 6.25 kg of silica gel (Matrex Silica Si, particle size 20–45 mm, pore diameter 60 Å, from Amicon Corp., USA). The column temperature was 50° C. The column was then washed with 30 l of a mixture of hexane:isopropanol, 90:10, in order to remove all nonpolar lipids.

The galactolipid material was then eluted from the column with 20 l of a mixture hexane:isopropanol, 60:40, giving a galactosyldiacylglycerol fraction. Evaporation of this fraction gave about 700 g of DGDG, the major lipid class. The galactolipid material was then dispersed in water and subjected to freeze-drying, which resulted in a free-flowing powder.

Enrichment of DGDG from galactolipids 50 g galactolipids from oats, as obtained above, having a content of DGDG of about 70%, were dissolved in 250 ml hexane: isopropanol, 70:30, giving a total amount of 300 ml. The solution obtained was loaded on a silica gel (110 g) column and the less polar constituents were eluted with 1 l of the mixture of hexane:isopropanol, 70:30. The enriched DGDG fraction was eluted with 2 l acetone. The acetone fraction was evaporated and freeze-dried. The total yield was 17 g of an almost pure DGDG product.

Hydrogenation of galactolipids 200 g of a galactolipid mixture obtained from oats as stated above was dissolved in 2 l warm isopropanol. 15 g of a palladium on carbon catalyst (Pd 15%, moisture 53%, Engelhard Rome s.r.i., Italy) was placed in the bottom of a pressure reactor (Model No. 4552M; Parr Instrument Co., USA) equipped with two impellers on a stirrer shaft. The solution was then transferred into the reactor under a seal of nitrogen to reduce the fire hazard. The reactor vessel was sealed and first pressurized three times with nitrogen in order to remove air and then three times with hydrogen gas (Plus 4.5, from AGA Gas AB, Sweden). The hydrogen pressure was then kept at 6 bars, the stirrer set at 600 rpm and the mixture was heated to 70° C. It took 14 minutes for the reaction mixture to reach its temperature setpoint. The hydrogenation process was conducted for 6 hours after which the reaction product was filtered through a 0.45 μm filter in order to remove carbon particles and palladium. Solvent was evaporated on a rotavapor, the residual solid material was dispersed in 1600 ml of deionized water and freeze-dried.

The yield of hydrogenated galactolipids after filtration and freeze-drying was 155 g. The hydrogenation performance was evaluated by gas chromatography; only saturated fatty acids could be detected in the hydrogenated product.

Galactolipids from wheat gluten 1 kg of wheat gluten powder (AB Skånebrännerier, Sweden) was extracted with 4 l of 95% ethanol at 70° C. for 3 h in a beaker. The slurry was then filtered under a pressure of 400–500 kPa and the filtercake obtained was washed with 1 l of warm 95% ethanol. The combined ethanol solutions were evaporated at maximum 60° C. and gave about 60 g of a yellow oil.

The oil was applied to a stainless steel column containing 45 g of silica gel (Matrex Silica Si, particle size 20–45 μm, pore size 60 Å, from Amicon Corp., USA). The column was then washed with 700 ml of a mixture hexane:isopropanol, 90:10, in order to remove neutral lipids.

In order to remove MGDG and some other polar lipids the column was subsequently washed with 1000 ml of a mixture hexane: isopropanol, 70:30. Elution of DGDG was carried out with 1000 ml of pure acetone. After evaporation about 4 g of an almost pure DGDG product was obtained.

Galactolipids from rye 100 g rye flakes (Kungsörnen AB, Sweden) were stirred for 60 min in a mixture of industrial hexane and isopropanol, 90:10. The slurry was filtered and evaporated which gave 0.5 g polar lipids. The residue, dissolved in 10 ml of a mixture of hexane and iso-propanol, 70:30, was loaded on three Sep-pak Silica plus columns (Millipore Corp., USA) connected in series, washed with 20 ml of the same mixture of solvents and eluted with 15 ml acetone. The eluate was evaporated and freeze-dried and the yield was 47 mg of galactolipids.

Chemical and physical characterization of different galactolipid materials

Lipid class analysis

Lipid class analysis was performed by high performance liquid chromatography, HPLC, using a column packed with diol-modified silica (LiChrosphere 100 DIOL, 5 μm, 250 mm×4 mm i.d.; E. Merck, Germany). The column was enclosed in a water bath held at 75° C. The analytical system consisted of a HPLC pump CM 4000 (LDC/Milton Roy, USA), and an injector, model 7125, with a 20 μl injection loop (Rheodyne Inc., USA). The evaporative light-scattering detector used was a Sedex 45 (S.E.D.E.R.E., France) equipped with a Sedex 55 nebulisation chamber with a drift tube temperature and air inlet pressure of 97° C. and 2.0 bar, respectively.

The flow of the mobile phase was 1 ml/min during the analysis. A binary solvent gradient, linear over 25 min, was used starting with 100% of A and ending with 100% of B, where A=hexane:isopropanol:n-butanol:tetrahydrofuran:isooctane:water, 64:20:6:4.5:4.5:1, and B=isopropanol:n-butanol:tetrahydrofuran:isooctane:water, 75:6:4.5:4.5:10. All solvents contained ammonium acetate, 180 mg/l.

Data collection and processing were done with GynkoSoft Data system version 4.22 (Softron GmbH, Germany). Typical amount injected for analysis was 100 μg. Identification was based on retention time comparison with authentic standards (Karlshamns LipidTeknik AB, Sweden). Volatile compounds were not detected in this system. Quantification was based on peak area calculations.

Zeta potentials were determined on dilute aqueous galactolipid dispersions with a Zetasizer 4 instrument (Malvern Instruments Ltd., UK)

TABLE 1

Characterisation of different galactolipid materials

|  | o-GL | o-h-GL | o-DGDG | w-GL | w-DGDG | r-GL |
|---|---|---|---|---|---|---|
| DGDG content, area % | 73 | 70 | 72 | 100 | 80 | 100 | 67 |
| Z-potential, mV | −74 | −76 | −30 | −51 | −75 | −38 | −37 |

In this Table 1 as well as in Table 2 below the following abbreviations are used o-GL=galactolipids from oats
o-h-GL=hydrogenated galactolipids from oats
o-DGDG=enriched galactolipids from oats
w-GL=galactolipids from wheat
w-DGDG=enriched galactolipids from wheat
r-GL=galactolipids from rye Fatty acid analysis Analysis of the fatty acid profile was done by gas chromatography after transesterification of the lipids to fatty acid methyl esters. These were separated and quantified by capillary column gas chromatography on a Varian 3500 Capillary Gas Chromatograph equipped with a capillary column 30 m×0.25 mm i.d. (DB-WAX; J&W Scientific, USA), an on-column injector and a flame ionization detector. Helium was used as the carrier gas. Integration was performed with GynkoSoft Data system version 4.22 (Softron GmbH, Germany). Transesterification was done by adding 1 mg of a lipid sample to 2 ml of dimethyl carbonate:isooctane, 1:1. 1 ml of a solution containing 2.3 g sodium dissolved in 200 ml of methanol was added and the test tube-was shaken vigorously for 30 s and left at room temperature for 15 min to ensure complete reaction. 3 ml water was added and the test-tube was shaken and then centrifuged at 2×g. 0.5 μl of the organic layer was injected on the chromatograph with the following separation conditions. The oven was temperature programmed, starting at 130° C. (2 min), increased to 150° C. (300/min) and 220° C. (3.2° C./min) with a 10 min hold. The injector temperature was 130° C. and the detector temperature was 250° C. Initially the gas flow was 2.7 ml/min. The results are expressed as normalized weight percentages using the external standard method. No correction factors are used for the minor constituents for which standards are not available or acceptably pure.

TABLE 2

Characterisation of fatty acid composition

| Fatty acid composition, weight % | o-GL | o-h-GL | o-DGDG | w-GL | w-DGDG | r-GL |
|---|---|---|---|---|---|---|
| C 14:0 |  |  |  |  | 1 |  |
| C 16:0 | 20 | 21 | 21 | 16 | 15 | 13 | 12 |
| C 18:0 | 1 | 1 | 74 | 2 | 1 | 1 |  |
| C 18:1 n-9 | 17 | 17 |  | 19 | 6 | 5 | 8 |
| C 18:1 n-7 | 1 | 1 |  | 1 | 1 | 1 | 1 |
| C 18:2 n-6 | 53 | 52 |  | 58 | 71 | 68 | 69 |
| C 18:3 n-3 | 2 | 2 |  | 3 | 3 | 3 | 5 |
| Minors <1% and unidentified | 6 | 6 | 5 | 1 | 3 | 8 | 5 |

NMR spectroscopy of digalactosyldiacylglycerols

One-dimensional proton-decoupled natural abundance $^{13}C$ NMR spectra were recorded on a Bruker AM-400 spectrometer (Bruker Analytische Messtechnik GmbH., Germany) at a $^{13}C$ frequency of 100.614 MHz. The pulse angle was 36°, the pulse repetition time 1.0 s and resolution 1.526 Hz per data point. 3 Hz line broadening was applied during processing. The samples (10–40 mg) were diluted in a mixture of 730 μl DMSO-$d_6$ (Aldrich Chemical Comp., Inc., USA) and 20 μl $D_2O$ (Aldrich Chemical Comp., Inc., USA) and transferred to an NMR tube (5 mm i.d.).

TABLE 3

$^{13}C$ Chemical shifts (ppm) of digalactosyldiacylglycerols from wheat and oats

| Signal | w-DGDG | o-DGDG |
|---|---|---|
| Fatty acid moieties |  |  |
| C(n) | 13.8 | 13.7 |
| C(n-1) | 21.9 | 21.9 |
| C(n-2) | 30.8 | 30.2 |
| C, methylene | 28.3–28.9 | 28.4–29.0 |
| C, allylic | 26.5 | 26.5 |
| C, doubly allylic | 25.1 | 25.1 |
| C, olefinic | 127.6–129.6 | 127.6–129.5 |
| C3 | 24.3 | 24.3 |
| C2 | 33.3, 33.5 | 33.3, 33.5 |

TABLE 3-continued

| 13C Chemical shifts (ppm) of digalactosyldiacylglycerols from wheat and oats | | |
|---|---|---|
| Signal | w-DGDG | o-DGDG |
| C1 | 172.2, 172.5 | 172.1, 172.4 |
| Glycerol moiety | | |
| sn-1 | 62.3 | 62.4 |
| sn-2 | 69.8 | 69.8 |
| sn-3 | 66.6 | 66.6 |
| Digalactosyl moiety | | |
| C1 (inner) | 103.6 | 103.6 |
| C1' (outer) | 99.4 | 99.4 |
| others | 60.4, 66.3, 67.7, 68.2, 68.6, 69.3, 70.1, 71.1, 72.8, 72.8 | 60.4, 66.3, 67.7, 68.2, 68.6, 69.3, 70.1, 71.1, 72.8, 72.9 |

EXAMPLES

Example 1

Formation of an aqueous gel

The galactolipid material prepared from oats was mixed with different amounts of water in order to test the swellability in water. Lipid-water samples were prepared by weight in glass tubes. The samples were alternately-mixed with a rod and centrifuged at room temperature until apparently homogeneous systems were formed. The samples were inspected as to physical appearance after storing for six months at room temperature. The lamellar liquid crystalline phase was detected by polarising light microscopy. The results are summarised in the following table:

| Galactolipid material, % | Appearance |
|---|---|
| 1.0 | Fine dispersion; slight sedimentation |
| 4.8 | Fine dispersion; slight sedimentation |
| 10.5 | Lamellar + aqueous phase in equal volumes |
| 19.3 | Lamellar + aqueous phase; the aqueous phase <10% by volume |
| 24.8 | Lamellar phase |
| 45.0 | Lamellar phase |

This means that a homogeneous single phase gel was formed at a galactolipid content of about 25% and higher.

Example 2

Viscosity properties of an aqueous gel

A galactolipid gel containing 55% water was prepared according to Example 1. Viscosity measurements were carried out with a Bohlin VOR rheometer (Bohlin Reologi AB, Sweden) equipped with a concentric cylinder (C14; torque element: 91 gcm) at different shear rates and temperatures. The viscosity was measured 24 h after preparation. Steady-flow viscosity values (in Pas) are summarised below:

| Shear rate, 1/s | 20° C. | 40° C. | 60° C. |
|---|---|---|---|
| 0.292 | 98.8 | 84.5 | 77.0 |
| 0.581 | 65.7 | 54.5 | 42.1 |
| 2.312 | 46.0 | 34.0 | 19.5 |
| 9.207 | 37.4 | 29.6 | 15.0 |

It was concluded that the sample was shear-thinning (pseudo-plastic), i.e. the viscosity was dependent on the shear rate, a rheological behaviour typical for lamellar liquid crystalline phases. Furthermore, an increase in temperature resulted in only a slight decrease in viscosity, indicating the absence of phase transitions within the investigated temperature range. After storing the gel for 18 months at room temperature it was visually inspected. No microbial growth could be observed. The physical appearance did not change during the storage, which is remarkable since no precautions were taken regarding storage temperature, antioxidants, preservatives, etc.

This reflects the excellent stability of the galactolipid material even in an aqueous environment which could cause, e.g. hydrolysis of the acyl chains or microbial degradation.

Example 3

Release test

In vitro release tests of a water-soluble dye, methylene blue (E. Merck, Germany), were performed on galactolipid and phospholipid gels initially containing 60% lipid and 50 mM methylene blue. The galactolipid material was prepared from oats. The phospholipid was chromatographically purified phosphatidylcholine from soybean (s-PC; Karlshamns LipidTeknik AB, Sweden). The diffusion medium was membrane-filtered water equilibrated at 37° C. The diffusion cell consisted of a membrane tubing made of regenerated cellulose (Spectra/Por; molecular weight cut-off: 6,000–8,000; flat width: 1.0 cm) containing about 2.5 g of gel. The tubing was immersed into a thermostated beaker (i.d. 10 cm), containing 250 g medium, at a fixed position approximately 3 cm from the bottom. The beaker was placed on a magnetic stirrer with a rotating speed of 200 rpm. Aliquots of medium were withdrawn at selected times and analysed spectrophotometrically at 665 nm. As a reference, the release of methylene blue from a cellulose tubing containing a 50 mM methylene blue aqueous solution was also measured.

After 2.5 h no detectable release of dye from the galactolipid gel could be detected, whereas 1.3% was released from the s-PC gel. After 5 h the galactolipid gel had released only 0.13% of its dye content, which was approximately 11 times less than that from the s-PC gel.

This indicates that the galactolipid formulation would result in a slow release of a bioactive material when administered in vivo and would thus be useful as a depot formulation.

Example 4

Release test

An in vitro release test of a water-soluble drug, remoxipride hydrochloride monohydrate (Astra AB, Sweden), was performed on a galactolipid gel initially containing 60% lipid, 15% remoxipride hydrochloride and 25% water.

The diffusion medium was a phosphate buffer (pH 7.4; ionic strength 0.05 M) equilibrated at 37° C. The diffusion cell consisted of a membrane tubing made of regenerated cellulose (Spectra/Por 3; molecular weight cut-off: 3.500; flat width: 1.0 cm; length 4 cm) containing about 1 ml of gel. The tubing was closed at both ends with weight-clamps and placed on the bottom of a thermostated dissolution bath (Sotax AT 6; i.d. 10 cm), containing 600 ml phosphate buffer. The buffer solution was stirred by a rotating paddle at a speed of 50 rpm. A sample of 1 ml was withdrawn at preselected times and analysed. The sample was replaced with 1 ml of buffer. The concentration of remoxipride was determined by reversed-phase liquid chromatography with a $\mu$-Bondapak C18 column. The eluent used was a mixture of phosphate buffer pH 1.8 and acetonitrile, 4:1. A spectrophotometric detector was used and the wavelength was 254 nm.

The gel gave rise to a surprisingly slow release of the incorporated drug. After 2 h less than 2% of the incorporated drug was released from the galactolipid gel. Approximately 3% was released after 4 h.

This suggests that the galactolipid formulation is suitable as a parenteral depot for sustained release of a bioactive material, here exemplified by remoxipride hydrochloride.

Example 5

Formation of liposomes

Liposomes, that is multilamellar vesicles, were prepared and characterised in the following way. Water was added to galactolipids from oats to give final concentrations of 1.0 and 10.0% lipid. The samples were allowed to equilibrate at room temperature for 24 h during gentle agitation giving liposomal dispersions.

In order to prepare unilamellar vesicles a part of the dispersion was transferred to a glass tube and disrupted by an ultrasonicator (XL-2020; Heat Systems Inc., USA), equipped with a microtip probe, over nitrogen at 0° C. The following settings were used: output control 3.5, process time 3×2 min, pulse off time 2×4 min.

Particle size distribution of the resulting liposomal dispersions was determined by dynamic light scattering (Zetasizer 4, Malvern Instruments, UK) at an angle of 90° and at room temperature, using a ZET5110 sizing cell and multimodal analysis. The following results, reported as Z averages, were obtained:

|  | Size, nm |
| --- | --- |
| Before sonication | |
| 1.0% dispersion | 467 |
| 10.0% dispersion | 551 |
| After sonication | |
| 1.0% dispersion | 144 |
| 10.0% dispersion | 148 |

The resulting dispersions before and after ultrasonication were studied with an optical microscope (40–100x, Olympus CH-2, Japan). A small amount of the liposomal dispersion was put onto a glass slide. The appearance of the sample was then observed between crossed polarizers. Only the non-sonicated liposomes could be observed, having the characteristic shape of Malthesian crosses. The ability of the galactolipids to form vesicles was also confirmed by freeze-fracture transmission electron microscopy.

These results show the excellent ability of the galactolipids to form multilamellar vesicles, using the simple direct hydration method, without addition of volatile organic solvents or co-surfactants. Small unilamellar vesicles are then easily formed by ultrasonication, as described above, or by any conventional means, e.g. by extrusion through a polycarbonate membrane.

Example 6

Encapsulation efficiency

The encapsulation efficiency of an incorporated dye in vesicles of the galactolipid material prepared from oats was investigated. The galactolipid material was directly hydrated in a 20 nM fluorescein aqueous solution at a concentration 4.8%. The dispersion was allowed to swell for 24 h at room temperature.

The dye-loaded vesicles were separated from the non-incorporated dye by gel filtration on a Sephadex G 50 column (height 60 cm, i.d. 1.5 cm) at room temperature. An EDTA buffer (1 mM EDTA, 5 mM Tris, 150 mM NaCl), adjusted to pH 7.4, was used as eluent. A concentrated dye loaded liposome-dispersion was introduced into the column bed, followed by the buffered EDTA solution. The column eluent was continuously monitored at 240 nm by a UV spectrophotometer equipped with a microflow cell and a chart recorder and collected in an automatic fraction collector. Two fractions, the dye-loaded vesicles and the untrapped dye solution, were collected separately and adjusted to defined volumes. The dye concentrations were determined spectrophotometrically at 285.2 nm, and from these data the captured volume and encapsulation efficiency were calculated. The following results were obtained: Captured volume 2.1 $\mu$l/mg lipid and encapsulation efficiency 11%. The vesicle size was determined to be 509 nm (Z average).

Direct hydration of the galactolipids results in the formation of multilamellar vesicles, as described in Example 5. The data above indicate that these vesicles have a much higher captured volume and a better encapsulation efficiency than conventional vesicles based on phospholipids, which are reported to have a captured volume of approximately 0.5 $\mu$l/mg lipid.

The direct hydration method for producing multilamellar vesicles is a technically simple and fast method and thus industrially applicable. By applying this method on the galactolipid material it is also possible to obtain a much higher captured volume, that is a much better encapsulation efficiency, which previously has been the major disadvantage when using phospholipids for the production of multilamellar vesicles.

Example 7

Formation of aqueous dispersions

Enriched galactolipid material, DGDG, from oats was mixed with water in order to test the swellability in water. Lipid-water samples were prepared as described in Example 1. The results are summarised in the following table:

| Enriched galactolipid, % | Appearance |
| --- | --- |
| 1.1 | Fine milky dispersion |
| 9.6 | Slightly viscous milky dispersion |
| 21.2 | Viscous milky dispersion |

As with the non-enriched material, the swellability in water of the enriched material was extremely good and homogenous dispersions were easily formed.

Example 8

Formation of aqueous dispersions

Hydrogenated galactolipid material from oats was mixed with water in order to test the swellability in water. Lipid-water samples were prepared as described in Example 1.

| Hydrogenated galactolipid, % | Appearance |
|---|---|
| 1.3 | Fine white dispersion |
| 5.7 | Slightly viscous white dispersion |
| 10.2 | Viscous white dispersion |

As with the non-hydrogenated material, the swellability in water of the hydrogenated material was extremely good. This material contains only saturated fatty acid residues which means that it gives rise to a highly ordered, crystalline structure, both in the dry state and in the presence of water. The chain melting point of the hydrogenated material as a dispersion in water was approximately 55° C. as determined by differential scanning calorimetry. The corresponding value for a non-hydrogenated material was well below 0° C.

Example 9

Preparation of water-free viscous dispersion

Viscous dispersions were prepared according the following recipes:

| Ingredient | % |
|---|---|
| Galactolipids | 10.0 |
| Glycerol, 99% | 90.0 |
| Galactolipids | 20.0 |
| Glycerol, 99% | 80.0 |

The galactolipids, prepared from oats, and glycerol were alternately mixed with a rod and centrifuged at room temperature until highly viscous, homogeneous and apparently isotropic liquids were formed. Both liquids consisted of a dispersion of a lamellar phase in glycerol, i.e. multilamellar vesicles, according to their textures in the polarising light microscope. The samples were inspected as to physical appearance after storing for one year at room temperature. No sedimentation could be observed, irrespective of galactolipid concentration, indicating that the glycerol had a stabilising effect on the vesicle dispersion.

Example 10

Preparation of a water-free formulation for use in the improvement of mucosal condition Sulfhydryl-containing agents like DL-cysteine and N-acetyl-L-cysteine may stimulate the healing and prevent recurrence of duodenal ulceration in man. Gastric ulcers may be produced by. ischaemia or noxious substances like ethanol and acetylsalicylic acid, which damage and remove the duodenal mucosa.

A formulation was prepared using the following ingredients:

| Ingredient | % |
|---|---|
| Galactolipids from oats | 10.0 |
| N-acetyl-L-cysteine | 10.0 |
| Glycerol, 99% | 80.0 |

N-acetyl-L-cysteine was dissolved in glycerol during gentle agitation and heating to about 60° C. in an open beaker. The galactolipid material was then added, and the resulting apparently clear liquid was transferred to a glass container with a plastic cap. The preparation, a dispersion as revealed from polarising light microscopy, was stored in the refrigerator for more than 6 months.

Glycerol was chosen as a solvent since sulfhydryl-containing substances like N-acetyl-L-cysteine are unstable in aqueous solution and may be transformed into substances which have no pharmacological effect on the mucosa.

The galactolipid material is beneficial on its own, since in vivo studies in rats have shown that it has a protective effect on the gastric mucosa.

Different topical formulations with hydrocortisone, an anti-inflammatory drug, were prepared as described in Examples 11–14. The galactolipid material was prepared from oats. All formulations were stable for more than 2 months at room temperature.

Example 11

| Ingredient | % |
|---|---|
| Galactolipids | 10.3 |
| Hydrocortisone | 1.0 |
| Water | 88.7 |

Hydrocortisone and the galactolipids were mixed well on a vortex mixer. After addition of water the formulation was alternately vortexed, centrifuged and gently heated until a fine milky dispersion was obtained.

Example 12

| Ingredient | % |
|---|---|
| Galactolipids | 22.1 |
| Hydrocortisone | 1.2 |
| 1-Propanol | 16.1 |
| Water | 60.6 |

Hydrocortisone was dissolved in 1-propanol during gentle heating and mixing. After addition of water and the galactolipids, the mixture was alternately vortexed, centrifuged and gently heated until an opaque, highly viscous gel was obtained.

Example 13

| Ingredient | % |
| --- | --- |
| Galactolipids | 18.9 |
| Hydrocortisone | 0.8 |
| 1,2-Propanediol | 26.3 |
| Water | 54.0 |

Hydrocortisone was dissolved in 1,2-propanediol during gentle heating and mixing. After addition of water and the galactolipid material, the mixture was alternately vortexed, centrifuged and gently heated until a yellowish, almost transparent gel was obtained.

Example 14

| Ingredient | % |
| --- | --- |
| Galactolipids | 26.8 |
| Hydrocortisone | 1.2 |
| Ethanol | 20.7 |
| Water | 51.3 |

Hydrocortisone was dissolved in ethanol during gentle heating and mixing. After addition of water and the galactolipids, the mixture was alternately vortexed, centrifuged and gently heated until a light brownish, transparent gel was obtained.

In Examples 15–17 different water-free topical preparations with are described. Again, hydrocortisone was chosen as model drug. The galactolipids were prepared from oats. All preparations were stable for more than 2 months at room temperature.

Example 15

| Ingredient | % |
| --- | --- |
| Galactolipids | 7.0 |
| Hydrocortisone | 0.8 |
| Glycerol, 99% (w/w) | 92.2 |

The galactolipids were dispersed in glycerol. After receiving a homogenous gel-phase, hydrocortisone was added. The mixture was gently heated and then mixed on a vortex mixer. The resulting formulation, a suspension, was a yellowish, viscous gel containing finely dispersed solid hydrocortisone particles.

Example 16

| Ingredient | % |
| --- | --- |
| Galactolipids | 13.5 |
| Hydrocortisone | 1.1 |
| Glycerol, 99% (w/w) | 85.4 |

The formulation was prepared according to Example 15. The resulting formulation was an opaque, highly viscous gel with a light yellow colour.

Example 17

| Ingredient | % |
| --- | --- |
| Galactolipids | 21.8 |
| Hydrocortisone | 1.1 |
| Propanol | 14.5 |
| Glycerol, 99% (w/w) | 62.6 |

Hydrocortisone was partly dissolved in propanol during gentle heating and mixing. After addition of the galactolipids and vigorous mixing, glycerol was added. The formulation was then vortexed, centrifuged and heated until a yellowish gel-like phase was formed. The gel contained finely dispersed hydrocortisone particles.

Example 18

An antifungal formulation for vaginal administration

| Ingredient | % |
| --- | --- |
| Galactolipids | 45.6 |
| Miconazole nitrate | 1.6 |
| Water | 52.6 |

Miconazole nitrate and the galactolipids, prepared from oats were mixed well on a vortex mixer. After addition of water the formulation was alternately vortexed and stirred until a brownish, homogenous and highly viscous gel was obtained.

Example 19

An antibacterial formulation as a wound dressing

| Ingredient | % |
| --- | --- |
| Galactolipids | 42.8 |
| Doxycycline hydrochloride | 1.7 |
| Water | 55.5 |

Doxycycline hydrochloride was dissolved in water to give a yellow solution. After addition of the galactolipids, prepared from oats, the mixture was alternately vortexed and stirred until a light brownish, highly viscous gel was obtained.

Example 20

An antibacterial formulation for administration to the external auditory canal

| Ingredient | % |
| --- | --- |
| Galactolipids | 2.0 |
| Doxycycline hydrochloride | 2.0 |
| Water | 96.0 |

Doxycycline hydrochloride was dissolved in water to give a yellow solution. After addition of galactolipids, prepared from oats, the mixture was vortexed until a yellow and milky doxycycline-loaded vesicle dispersion was obtained.

Example 21

An antidiabetic formulation for nasal administration

| Ingredient | % |
| --- | --- |
| Galactolipids | 3.5 |
| Insulin solution, 100 IU/ml (Actrapid Human, Novo Nordisk AS, Denmark) | 96.5 |

The galactolipids, prepared from oats, were hydrated in the commercial insulin solution during gentle agitation for 24 h. The resulting dispersion was transferred to a conventional nasal pump flask by which a fine aerosol spray could be generated.

Example 22

A spermaticidic formulation

| Ingredient | % |
| --- | --- |
| Galactolipids | 22.5 |
| Nonoxynol | 5.0 |
| Water | 72.5 |

A mixture of the three components was alternately vortexed, centrifuged and gently heated until a light brownish, transparent gel was obtained.

Example 23

An analgesic formulation for rectal administration

| Ingredient | % |
| --- | --- |
| Galactolipids | 43.4 |
| Paracetamol | 2.9 |
| Water | 53.7 |

Galactolipids prepared from oats and paracetamol were mixed well. After addition of water, the formulation was alternately mixed with a rod, gently heated and than centrifuged at room temperature until a yellow-brown, highly viscous gel was obtained.

The viscosity of the galactolipid formulations are not significantly affected by moderate temperature changes. A formulation kept in the refrigerator is easily transferred to a syringe or similar device and may then be administered rectally and subsequently heated to body temperature, without loosing its viscosity or consistency.

Example 24

An antiglaucoma formulation for ocular administration

| Ingredient | % |
| --- | --- |
| Galactolipids | 1.00 |
| Timolol maleate | 0.34 |
| Water | 98.66 |

The galactolipids, prepared from oats, were dispersed in one portion of the water and allowed to swell overnight during gentle agitation at room temperature. Timolol maleate, dissolved in the rest of the water, was then added and the resulting liposomal dispersion was transferred to a glass tube and disrupted by an ultrasonicator (XL-2020; Heat Systems Inc., USA; output control 4), equipped with a microtip probe, over nitrogen at 0° C. for 10 min.

This resulted in a clear dispersion, containing small unilamellar vesicles and a drug in a pharmacologically effective amount, to be used as an eye drop formulation. The galactolipids provide both for an increased viscosity of the formulation, as well as an improved bioadhesivness, which may result in a better bioavailability of the drug due to prolonged residence time on the cornea.

Example 25

Incorporation of the lithium salt of gammalinolenic acid into galactolipid liposomes A liposomal galactolipid formulation with the lithium salt of gammalinolenic acid, an anticancer drug, was prepared as follows.

| Ingredient | % |
| --- | --- |
| Li-GLA | 1.5 |
| Enriched galactolipid | 10.0 |
| 2.3% glycerol in water | ad 100.0 |

LI-GLA, with a gammalinolenic acid content of 75%, was obtained from Callanish Ltd. Scotland. The enriched galactolipid material, prepared from oats, and Li-GLA were mixed together and then the 2.3% glycerol solution was added. The mixture was left to hydrate (or swell) for 8 h. After high shear mixing at 12,000 rpm for 30 s, the liposomal dispersion was homogenised at 86 MPa for 3 min (EmulsiFlex-C30, Avestin Inc., Canada). A Li-GLA concentration of 1.5% corresponds to 53 mM.

The haemolytic effect of the liposomal dispersion was tested in vitro, as reported below under Test 6.

Example 26

Preparation of a dispersion containing 10% of L-tyrosine.

A dispersion was prepared in the following way:

| Ingredient | % |
|---|---|
| Galactolipids from oats | 6.4 |
| L-tyrosine | 10.0 |
| Water | 83.6 |

All ingredients were blended and submitted to high shear mixing at 15,000 rpm for 4 min to form a homogenous dispersion. The dispersion formed was stable for several weeks after preparation.

Biological tests

Test 1. Cutaneous irritation in vivo

Figure 1:
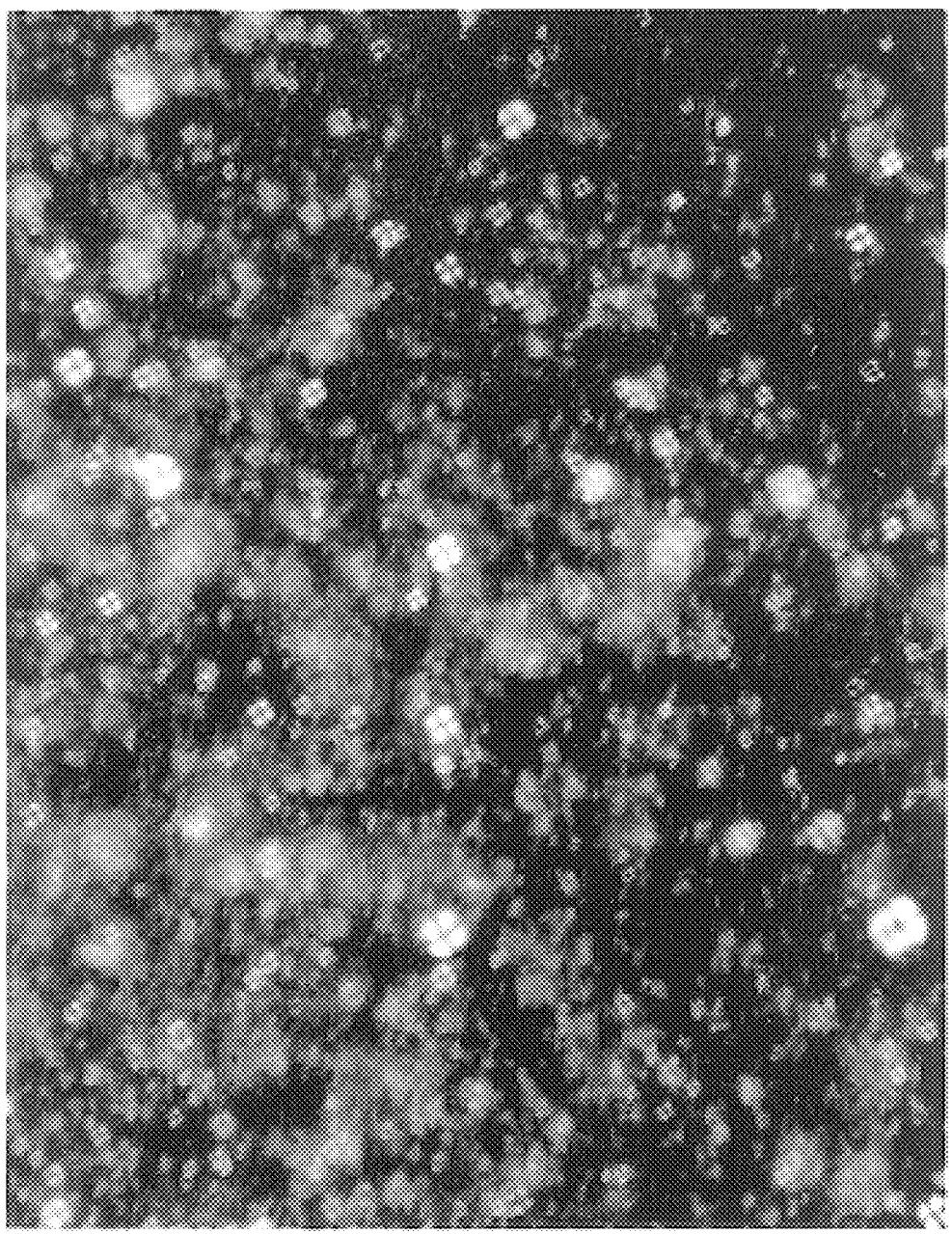
FIG. 1 shows a microphoto pattern in polarized light of liposomes prepared in Example 9 from 10% (w/w) galactolipids in glycerol in a magnification of ×100. The spherical shapes with the Malthesian crosses are characteristic features of liposomes.

In order to evaluate the skin toxicity of the galactolipids of the invention the following test was performed.

Galactolipids from oats were mixed with water for injection to a 10% gel and applied at a dose level of 0.5 ml per animal to the intact skin of 6 New Zealand White male rabbits and kept under semiocclusive bandage for 4 hours. A cutaneous examination for erythrema and oedema was then performed 1, 24, 48 and 72 hours after the removal of the bandage. Mean values were then calculated from the evaluation of the cutaneous lesions at 24, 48 and 72 h. The results are given in Table 5 below.

TABLE 5

Cutaneous irritation in rabbits

| | Erythema | Oedema |
|---|---|---|
| 24 h | 0 | 0 |
| 48 h | 0 | 0 |
| 72 h | 0 | 0 |

From this can be concluded that the application of a galactolipid gel does not provoke any noticable irritation.

Test 2. Evaluation of clearance of galactolipid liposomes in vivo

Preparation of $^3$H-fatty acid labeled DGDG

An amount of 500 mg of galactolipids from oats was tritium-labeled by catalytic reduction of the double bonds in the fatty acid moieties with tritium gas (Amersham Tritium Labeling Service, UK). The specific activity was 30–60 Ci/mmol per double bond reduced. $^3$H-DGDG was purified by two-dimensional thin-layer chromatography on silica gel 60 plates. The mobile phases were in the first direction chloroform:methanol:water, 65:25:4 (v/v), and in the second direction chloroform:methanol: acetic acid: water, 85:15:10:3.5 (v/v). The DGDG spot was eluted sequentially with chloroform:methanol:water, 65:25:4 (v/v), and 50:50:10 (v/v), pure methanol and methanol:water, 1:1 (v/v). The proportion of $^3$H in the lipophilic part of the galactolipid molecule was determined as follows: 18 nCi of $^3$H-labeled DGDG and 2 mg unlabeled material were subjected to alkaline hydrolysis in 1 ml 1 M KOH at 60° C. for 4 h. After neutralization with 0.2 ml 5 M HCl, 5 ml chloroform, 1.5 ml ethanol and 2.5 ml water were added. In this two-phase distribution 97% of the radioactivity was recovered in the lower (chloroform) phase.

Unlabeled galactolipids and $^3$H-DGDG at a total concentration of 2.0% (w/w) were dispersed in 2.5% (w/w) glycerol in water. The liposomal dispersion was equilibrated for 36 h at 4° C. It was then sonicated with a microtip probe for 3×2 min, pulse off time 4 min, over nitrogen at 0° C.

Test on rats

Fasted male Sprague Dawley rats, weighing approximately 250 g, were anaesthetized with diethylether. 0.5 ml of the sonicated dispersion, with a radioactivity of 1.8–2.7 µCi, was injected into the external jugular vein. The animals were sacrificed through aorta puncture at 2 min; 15 min, 60 min, 4 h and 20 h. Lipids in liver and blood plasma samples were extracted with chloroform:methanol, 1:1 (v/v). The extracts were dried under nitrogen, redissolved in chloroform and subjected to thin-layer chromatography on silica gel 60 plates developed in chloroform: methanol:water:acetic acid, 65:25:4:4 (v/v). The DGDG spot was scraped into counting vials; 1 ml of methanol: water, 1:1 (v/v), was added and the mixture was vortexed before adding 10 ml of toluene:Instagel (Packard Instruments B.V., The Netherlands), 1:1 (v/v). Radioactivity was determined in a Packard TriCarb liquid scintillation counter. Data are expressed as % injected dose of $^3$H-DGDG in 10 ml blood plasma (4% of total body weight) and whole liver at different times and are summarized in the table below.

Table 6

Percentage of injected $^3$H-DGDG left in 10 ml blood plasma (4% of total body weight) and liver at different times. Data are presented as mean ± standard deviation (n=3).

TABLE 6

Percentage of injected $^3$H-DGDG left in 10 ml blood plasma (4% of total body weight) and liver at different times. Data are presented as mean ± standard deviation (n = 3).

| | 2 min | 15 min | 60 min | 4 h | 24 h |
|---|---|---|---|---|---|
| Plasma | 57.8 ± 9.0 | 47.7 ± 5.4 | 17.4 ± 1.9 | 2.0 ± 0.4 | 0.04 ± 0.04 |
| Liver | 9.9 ± 2.2 | 17.2 ± 2.2 | 13.0 ± 1.6 | 2.1 ± 0.5 | 0.16 ± 0.03 |

The results suggest that vesicles comprising DGDG have a half-life of about 30 min when injected intravenously to rats. Furthermore it is evident that the galactolipid vesicles are cleared from the bloodstream and efficiently degraded, mainly by the liver.

Test 3. Formulations with a local anaesthetic drug and in vivo studies of spinal anaesthesia in rats Different formulations with bupivacaine hydrochloride, a local anaesthetic drug, were prepared as follows.

| Ingredient | Composition A % | Composition B % | Composition C % |
|---|---|---|---|
| Bupivacaine.HCl | 1.00 | 0.50 | — |
| Galactolipids | 10.00 | — | 10.00 |
| Glycerol, 99% | 2.57 | 2.48 | 2.59 |
| Water | 86.47 | 97.02 | 87.41 |

The ability of the formulations to extend the duration of effect of a local anaesthetic on the spinal cord and nerve roots was studied in a controlled experiment on rats chronically implanted with intrathecal catheters.

Four groups of male Sprague-Dawley rats (weight: 235–300 g) were studied one week after implantation of the intrathecal a catheter according to the method of T. L. Yaksh and T. A. Rudy (Physiol. Behav., 1976, Vol. 17, pp. 1031–1036). Two groups of rats received different doses of bupivacaine administered in a galactolipid formulation (Composition A), a third group received bupivacaine in an aqueous solution (Composition B), and a fourth group received the galactolipid formulation without any local anaesthetic (Composition C) according to the table below:

| Group | No. of rats | Composition | Injected volume, $\mu l$ | Injected amount of bupivacaine, $\mu g$ |
| --- | --- | --- | --- | --- |
| High dose | 7 | A | 20 | 200 |
| Law dose | 7 | A | 10 | 100 |
| Control | 8 | B | 20 | 100 |
| Placebo | 6 | C | 20 | 0 |

The rats were randomised to one of the four groups. The test substance was administered into the lower lumbar region of the dural sac via the implanted catheter. The effect of the test substance on locomotion was observed at regular intervals and graded according to a scale of 0, 1, 2, 3, and 4 where 0=no motor impairment and 4=paralysis of both hindlegs and forelegs. The rats were observed for at least 90 min.

Figure 2:
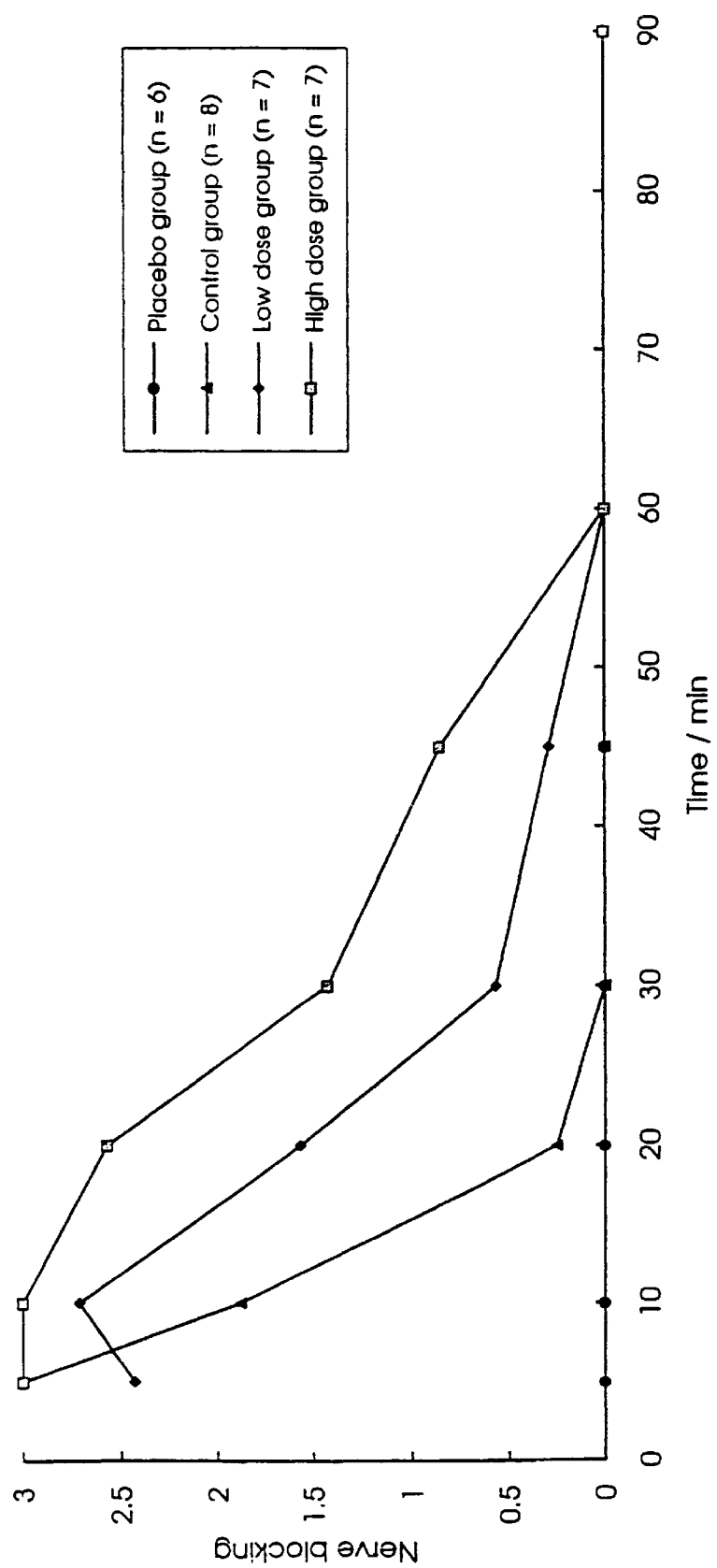
FIG. 2 shows the nerve blocking effect of a local anaestethic drug in a chronically implanted intrathecal rat model as described below in Test 3.

The results are summarised in FIG. 2. All animals receiving active local anaesthetic substance displayed a profound impairment of motor function early after dosing. However, the duration of this effect was noticeably different for the three groups, with the high dose group displaying the longest duration and control group the shortest duration of the paralysis. At 90 min all animals had recovered completely. The differences were statistically significant for the high dose group and the low dose group vs. the control group at 20 min (Wilcoxon's signed rank test). The high dose group was also different from the control group at 30 min. The placebo group did not show any effect at any time. No unexpected or toxic effects were seen and all effects were reversible.

Conclusion: The galactolipid formulation with bupivacaine could significantly extend the duration of the nerve blocking effect of bupivacaine in a chronically implanted intrathecal rat model. This further demonstrates that the galactolipid formulation is useful in prolonging the interaction of bioactive components.

Test 4. In vitro haemolysis test of liposomes containing Li-GLA

The haemolytic effect of the liposomal Li-GLA formulation prepared in Example 25, was tested and compared with free Li-GLA using human whole blood according to the following protocol.

Human blood from healthy volunteers was collected in 10 ml Vacutainer (Becton Dickinson, Canada) tubes containing 143 USP units of sodium heparin. 2 ml samples of blood were transferred to 25 ml Erlenmeyer flasks, each mixed with 1.0 ml test formulation diluted with 0.9% saline to yield the required test concentration. The samples were then incubated at 37° C. in an oxygen:carbon dioxide, 95:5, enriched atmosphere, 3 l/min, for 1 h, with constant gentle shaking. At the end of the incubation 10 $\mu l$ of the blood mixture was transferred to 500 $\mu l$ saline in a 1.5 ml Eppendorf tube. Standards giving 100% haemolysis were prepared by adding 10 $\mu l$ blood to 500 $\mu l$ pure water in a 1.5 ml Eppendorf tube. All samples were then spun for 2 min in an Eppendorf Microfuge (Brinkman Instruments Ltd, Canada) and finally analyzed on a centrifugal analyser (Cobas Bioanalyser; Hoffmann-La Roche Ltd, Canada) with UV scan of 540 nm. The results are presented below.

| Li-GLA concentration, mM | Haemolysis, % |
| --- | --- |
| 1.0 | 0.8 |
| 5.0 | 1.1 |
| 10.0 | 2.8 |
| 12.0 | 6.9 |
| 15.0 | 21.9 |
| 17.5 | 38.8 |

Li-GLA dissolved in 0.9% saline causes 100% haemolysis at a concentration of about 4–5 mM. Thus, the haemolytic activity of Li-GLA is greatly diminished in the liposomal form. The reduced haemolytic activity of liposomal Li-GLA has been confirmed by preliminary in vivo studies in rats; haemolysis is reduced by 50% to 80% when the liposomal formulation is used instead of the free Li-GLA. The liposomal formulation does not give rise to "red urine" in the rats while free Li-GLA does. In addition, it has been shown that the activity against cancer cells in vitro is almost identical with free Li-GLA and liposomal Li-GLA. These tests suggest that the liposomal galactolipid formulation reduces haemolysis, a serious side-effect, of the drug without affecting its pharmacological efficacy.

Conclusion

In conclusion our findings related to this invention are that lipid-polar solvent preparations based on the galactolipid material of the invention are superior to phospholipid preparations in all respects, such as physical stability of preparations, incorporation efficiency of drugs, and slow release capacity of incorporated drugs.

We claim:

1. A composition comprising a lipid-bilayer preparation formed of a galactolipid material extracted from cereals selected from the group consisting of wheat, rye, and oats,
   said galactolipid material containing at least about 50% by weight of digalactosyldiacylglycerol, and
   said bilayer preparation encapsulating an active ingredient selected from the group consisting of a cosmetic ingredient, pharmaceutical ingredient, and food ingredient.

2. The composition according to claim 1, wherein said galactolipid material contains about 70 to about 80% by weight of digalactosyldiacylglycerol.

3. The composition according to claim 1, wherein said galactolipid material further contains a mixture of monogalactosyldiacylglycerol and phosphatidylcholine.

4. A gel comprising:
   (1) a lipid-bilayer preparation formed of a galactolipid material extracted from cereals selected from the group consisting of wheat, rye, and oats,
   said galactolipid material containing at least about 50% by weight of digalactosyldiacylglycerol, and
   said bilayer preparation encapsulating an active ingredient selected from the group consisting of a cosmetic ingredient, pharmaceutical ingredient, and food ingredient; and
   (2) a polar solvent.

5. The gel according to claim 4, wherein the amount of said galactolipid material in said polar solvent is about 25 to about 90% by weight.

6. The gel according to claim 4, wherein said galactolipid material contains about 70 to about 80% by weight of digalactosyldiacylglycerol.

7. The gel according to claim 4, wherein said galactolipid material further contains a mixture of monogalactosyldiacylglycerol and phosphatidylcholine.

8. A liposome comprising:
(1) a lipid-bilayer preparation formed of a galactolipid material extracted from cereals selected from the group consisting of wheat, rye, and oats,
said galactolipid material containing at least about 50% by weight of digalactosyldiacylglycerol, and
said bilayer preparation encapsulating an active ingredient selected from the group consisting of a cosmetic ingredient, pharmaceutical ingredient, and food ingredient; and
(2) a polar solvent.

9. The liposome according to claim 8, wherein the amount of said galactolipid material in said polar solvent is about 0.01 to about 25% by weight.

10. The liposome according to claim 8, wherein said galactolipid material contains about 70 to about 80% by weight of digalactosyldiacylglycerol.

11. The liposome according to claim 8, wherein said galactolipid material further contains a mixture of monogalactosyldiacylglycerol and phosphatidylcholine.

12. A method for delivering a cosmetic, pharmaceutical or food composition to a mammal which comprises:

orally, enterally, parenterally, rectally, vaginally, topically, ocularly, nasally or aurally administering to a mammal a composition comprising a lipid-bilayer preparation formed of a galactolipid material extracted from cereals selected from the group consisting of wheat, rye, and oats,
said galactolipid material containing at least about 50% by weight of digalactosyldiacylglycerol, and
said bilayer preparation encapsulating an active ingredient selected from the group consisting of a cosmetic ingredient, pharmaceutical ingredient, and food ingredient.

13. The method according to claim 12, wherein said galactolipid material contains about 70 to about 80% by weight of digalactosyldiacylglycerol.

14. The method according to claim 12, wherein said galactolipid material further contains a mixture of monogalactosyldiacylglycerol and phosphatidylcholine.

15. A method for delivering a gel or a liposome to a mammal which comprises orally, enterally, parenterally, rectally, vaginally, topically, ocularly, nasally or aurally administering to a mammal a gel or liposome comprising:
(1) a lipid-bilayer preparation formed of a galactolipid material extracted from cereals selected from the group consisting of wheat, rye, and oats,
said galactolipid material containing at least about 50% by weight of digalactosyldiacylglycerol, and
said bilayer preparation encapsulating an active ingredient selected from the group consisting of a cosmetic ingredient, pharmaceutical ingredient, and food ingredient; and
(2) a polar solvent.

16. The method according to claim 15, wherein said gel comprises about 25 to about 90% by weight of said galactolipid material in said polar solvent.

17. The method according to claim 15, wherein said liposome comprises about 0.01 to about 25% by weight of said galactolipid material in said polar solvent.

18. The method according to claim 15, wherein said galactolipid material contains about 70 to about 80% by weight of digalactosyldiacylglycerol.

19. The method according to claim 15, wherein said galactolipid material further contains a mixture of monogalactosyldiacylglycerol and phosphatidylcholine.

* * * * *